United States Patent [19]
Champseix et al.

[11] Patent Number: 5,665,309
[45] Date of Patent: Sep. 9, 1997

[54] DEVICE FOR AGITATING AND FOR TAKING SAMPLES OF BLOOD PRODUCTS FROM TUBES WHICH ARE GROUPED TOGETHER IN RACKS

[75] Inventors: Henri Champseix, Montferreir Sur Lez; Serge Champseix, Teyran; Roger Le Comte, Carnon; Didier LeFevre, Saint Clement De Riviere, all of France

[73] Assignee: ABX, Montpellier Cedex, France

[21] Appl. No.: 597,969

[22] Filed: Feb. 7, 1996

[30] Foreign Application Priority Data

Feb. 7, 1995 [FR] France ................... 95 01397

[51] Int. Cl.⁶ .................................................. G01N 35/10
[52] U.S. Cl. ..................... 422/63; 422/65; 422/67; 422/100; 422/104; 436/43; 436/47; 436/54; 436/180; 366/211; 141/130; 141/329
[58] Field of Search ........................ 422/63, 65, 99, 422/100, 102, 103, 104; 436/43, 47, 48, 49, 54, 174, 180; 366/111, 114, 209–211

[56] References Cited

U.S. PATENT DOCUMENTS

| 4,387,076 | 6/1983 | Cabrera et al. .................. 422/67 |
| 4,475,411 | 10/1984 | Wellerfors ..................... 73/864.24 |
| 4,609,017 | 9/1986 | Coulter et al. .................. 141/1 |
| 4,921,678 | 5/1990 | Otani . | |
| 4,927,545 | 5/1990 | Roginski ..................... 210/745 |
| 4,928,539 | 5/1990 | Champseix et al. ............. 73/865.24 |
| 5,110,743 | 5/1992 | Windisch et al. ............. 436/48 |
| 5,472,669 | 12/1995 | Miki et al. .................... 422/63 |
| 5,525,298 | 6/1996 | Anami ........................... 422/63 |

FOREIGN PATENT DOCUMENTS

| 557828 | 9/1993 | European Pat. Off. . |
| 581984 | 2/1994 | European Pat. Off. . |
| 4117780 | 2/1994 | Germany . |
| 9205448 | 4/1992 | WIPO . |
| 9325885 | 12/1993 | WIPO . |

*Primary Examiner*—Long V. Le
*Attorney, Agent, or Firm*—Dennison, Meserole, Pollack & Scheiner

[57] ABSTRACT

A device for agitating and taking samples of blood products from tubes which are closed by stoppers and grouped together in a rack. The device includes a rack support adapted for holding at least one rack, at least one rack held by the rack support which is capable of holding a plurality of tubes with each tube being held in a selected position, a sampling station from which a sample of blood product can be withdrawn from a tube, a gripping device which is capable of taking hold and withdrawing from the rack one of the tubes at a selected position, bringing the tube to the sampling station and back to the selected position without agitation and replacing the tube in its selected position, and a drive device for displacing the gripping device. The device of the invention further includes a device for agitating the rack support and the rack which is operable during operation of the device for bringing and a device for withdrawing.

22 Claims, 7 Drawing Sheets

DEVICE FOR AGITATING AND FOR TAKING SAMPLES OF BLOOD PRODUCTS FROM TUBES WHICH ARE GROUPED TOGETHER IN RACKS

BACKGROUND OF THE INVENTION

The invention relates to hematologic analyzers which permit samples of blood products to be analyzed automatically.

It relates more particularly to a device for agitating and for taking samples of blood products from tubes which are closed by stoppers and which are grouped together in racks.

Before taking a blood product sample from a tube in order to subject it to analysis, it is essential to agitate the tube so as to mix the constituents of the product and thereby obtain a sample whose composition is homogeneous and representative of the product.

U.S. Pat. No. 3,231,244 discloses an automatic device for mixing blood products, said device comprising a rotary drum which is equipped with receiving seats which are capable of supporting tubes containing such products. The tubes are disposed radially with respect to the axis of rotation of the drum, such that their respective stoppers point outward. This is exclusively an agitating device, and it has the disadvantage that the tubes have to be loaded manually on the drum, and then withdrawn manually from the drum once agitation has been carried out.

Devices for agitating movable tube holders have also been available on the market for many years now. These tube holders have a U configuration in which the tubes are disposed side by side in non-predefined positions and are held by elastic means. This again is exclusively an agitating device, the principal disadvantage of which is that it necessitates manual operations, in particular with respect to loading the tube holders prior to agitation and unloading them after agitation.

Furthermore, EP-A-0,061,317 discloses a device for agitating and for taking samples of blood products, in which device the tubes containing the products are grouped together in racks, and the latter are disposed manually in a rotary drum. This drum has the function of ensuring, by means of rotation, the mixing of the blood products, and of immobilizing a rack in a substantially vertical position so that the tubes which it contains are immobilized with their stoppers facing downward. This device additionally comprises a sampling station which is displaceable in translation underneath the drum and parallel to its axis of rotation, this sampling station being equipped with a sampling needle which is able to take a sample from a tube in a rack after piercing the stopper of the tube, and to perform this sampling operation successively in a series of tubes. After analysis, the racks are withdrawn manually from the drum.

The principal disadvantage of this known device is that it cannot turn the drum, and thus agitate all the tubes, during the actual sampling operation itself. Moreover; the sampling station has to perform a multiplicity of translational displacements, in both directions, which fact leads to mechanical wear and tear. Furthermore, since the sampling is performed directly from a tube in a rack which is immobilized by the drum, it is necessary to provide strong, powerful mechanical members so that the drum remains completely immobile, in particular during the piercing of the stopper of each tube by the sampling needle.

A device for the transfer, agitation and sampling of blood products from tubes which are grouped together in racks is also known from the publication WO 93/25,885 of the Applicant, which device comprises a rotary support capable of holding a plurality of racks and of ensuring their mixing, by rotation, as well as a sampling station which is displaceable in translation and which is able to take a sample from a tube of a rack when the support is immobilized.

This device has basically the same disadvantages as those mentioned above, although, by contrast, it permits complete automation since it comprises transfer means which automatically load the racks on the rotary support with a view to taking samples, and automatically eject the racks from the rotary support after sampling.

Furthermore, U.S. Pat. No. 4,921,676 discloses a device for agitating and for taking samples of blood products from closed tubes which are grouped together in racks. The latter are brought one by one, without being agitated, into line with a mechanism which takes hold of the tubes contained in the rack individually, removes them from the rack, agitates them by partial rotation at a limited angle, and conveys them to a sampling station which is equipped with a needle, before replacing them in the rack.

The principal disadvantage of this device is that it does not agitate the products contained in the tubes for a sufficient length of time. Moreover, the structure and the kinematics of the mechanism for displacing the tubes are particularly complex, and its cost price is therefore high.

It must also be noted that all the devices mentioned above have the disadvantage that the analysis rates which they permit are not sufficiently fast from the point of view of the requirements of present-day laboratories.

SUMMARY OF THE INVENTION

Consequently, the object of the invention is to overcome the abovementioned disadvantages by proposing a device for agitating and for taking samples which, in particular, improves agitation of the products to be analyzed, permits faster processing speeds, makes it possible to reduce the mechanical wear and tear of the components, and requires less drive power.

To this end, the invention proposes a device for agitating and for taking samples of blood products from tubes which are closed by stoppers and which are grouped together in racks, of the type comprising a rack support capable of holding and of agitating at least one rack loaded with at least one tube, as well as at least one sampling station capable of piercing the stopper of the tube in order to remove the sample.

According to the invention, the device comprises gripping means which are capable of taking hold of and withdrawing at least one selected tube situated in a selected position in a selected rack which is held on the support; of bringing the selected tube or each selected tube, without agitating it, to the sampling station in order to remove a sample, and of replacing the selected tube or each selected tube in its position in the rack; as well as drive means capable of displacing the gripping means.

Thus, the selected tube or each selected tube is withdrawn from the rack in order to be conveyed to the sampling station and then be replaced in the rack. During the sampling operation, the rack support can continue to agitate the other tubes which it is supporting.

The piercing of the stopper of the tube is carried out each time on a tube which has been withdrawn from the rack, said rack still being held by the rack support, so that it is no longer necessrary, to provide high-powered mechanical means in order to hold the support in a stationary position, as was previously necessary.

According to another characteristic of the invention, the drive means are capable of displacing the gripping means into the following four successive positions:

rest position, in which the gripping means are remote from the rack support;

pick-up position, in which the gripping means are close to the selected tube or each selected tube and are capable of being activated in order to take hold of the selected tube or each selected tube;

sampling position, in which the gripping means are close to the sampling station in order to permit sampling from the selected tube or each selected tube; and depositing position, in which the gripping means are close to the rack support and are capable of being activated in order to release the selected tube or each selected tube and replace it in its position in the rack.

The gripping means advantageously comprise at least one pincer having at least two jaws which are capable of being brought together or moved apart from each other by means of an activator, for example a double-action pneumatic thrustor.

In a preferred embodiment of the invention, the gripping means are capable of approaching the selected tube or each selected tube in order to take hold of it in the rack, and of moving away from the selected tube or each selected tube after depositing it in the rack, by means of displacements in a general direction transverse to the axis of the tube. The gripping means thus act laterally with respect to the axis of the tube.

It is in this case advantageous if the tubes are held individually in the racks by means of U-shaped elastic clips which permit the tubes to be withdrawn or put back in place by means of a displacement parallel to these clips.

Alternatively, the displacements of the gripping means in approaching or moving away from the selected tube or each selected tube can be effected in the axis of the tube.

In an advantageous manner, the drive means effect the displacement of the selected tube by means of at least one translation, such that the tube retains substantially the same spatial orientation throughout its displacement. This displacement is preferably effected such that the stopper of the tube is turned downward. However, alternatively, this displacement can be effected such that the stopper of the tube is turned upward.

In a preferred embodiment of the invention, the rack support is in a fixed position in a hematologic analyzer, whereas the sampling station is displaceable in this hematologic analyzer, the drive means comprising first means for displacing the sampling station in translation in a general direction parallel to the direction of alignment of the tubes in the selected rack, and for bringing it into line with the selected tube, as well as second means for displacing the gripping means in a direction transverse to the direction of displacement of the sampling station.

Alternatively, the sampling station is in a fixed position in a hematologic analyzer, whereas the rack support is displaceable in this hematologic analyzer, the drive means comprising first means for displacing the rack support in a general direction parallel to the direction of alignment of the tubes in the rack, as well as second means for displacing the gripping means in a direction transverse to the direction of displacement of the rack support.

In another alternative, the rack support and the sampling station are both in fixed positions in a hematologic analyzer, the drive means being capable of displacing the gripping means in crosswise or orthogonal movements.

In a preferred embodiment of the invention, the rack support is mounted rotatably about an axis and comprises seats capable of receiving two racks disposed on either side of the axis, such that the tubes in one rack are oriented head-to-tail with respect to the tubes in the other rack.

According to another characteristic of the invention, means are provided for immobilizing the rack support in an off-position, which allows the gripping means to take hold of the selected tube or each selected tube of the selected rack prior to sampling and subsequently to replace it in the rack after sampling, the tubes in the rack having a defined orientation.

This defined orientation is advantageously substantially vertical, and the selected tube or each selected tube has its stopper directed downward.

According to another characteristic of the invention, the sampling station comprises a sampling needle which is displaceable in translation and has a tip capable of piercing the stopper of the selected tube, a first abutment capable of forming a bearing for the stopper of the selected tube in the sampling position, as well as a second abutment situated opposite the first abutment and capable of forming a bearing for the bottom of the selected tube when the latter is held in the sampling position by the gripping means.

The second abutment is advantageously adjustable in order to adapt to tubes of different lengths.

BRIEF DESCRIPTION OF THE DRAWINGS

In the description which follows, and which is given solely by way of example, reference is made to the attached drawings, in which.

DESCRIPTION OF THE PREFERRED EMBODIMENTS

Figure 1:
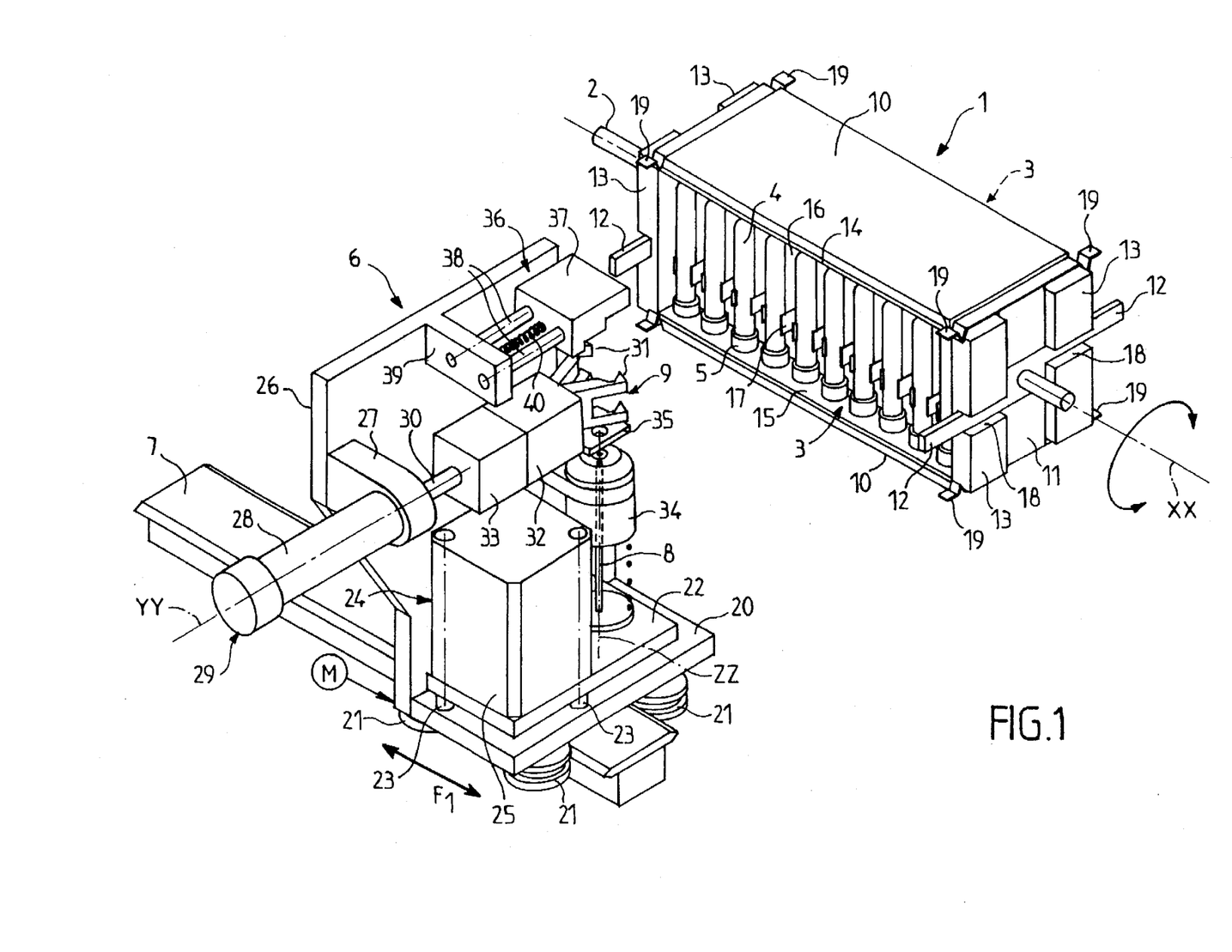
FIG. 1 is a perspective view of a device according to the invention in the rest position.
Figure 2:
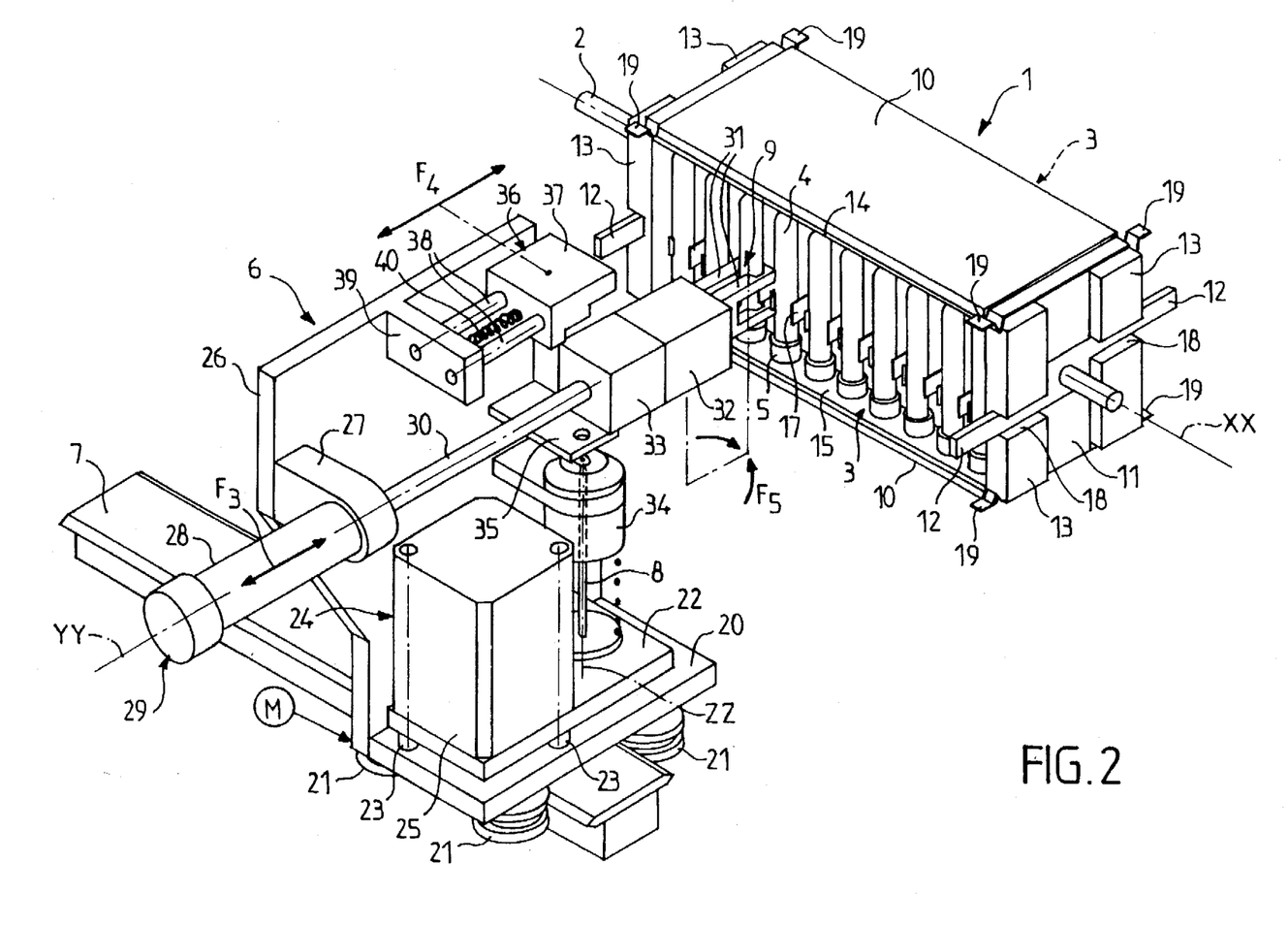
FIGS. 2 and 3 are views analogous to those in FIG. 1, the device being represented in the pick-up position and in the sampling position, respectively.
Figure 3:
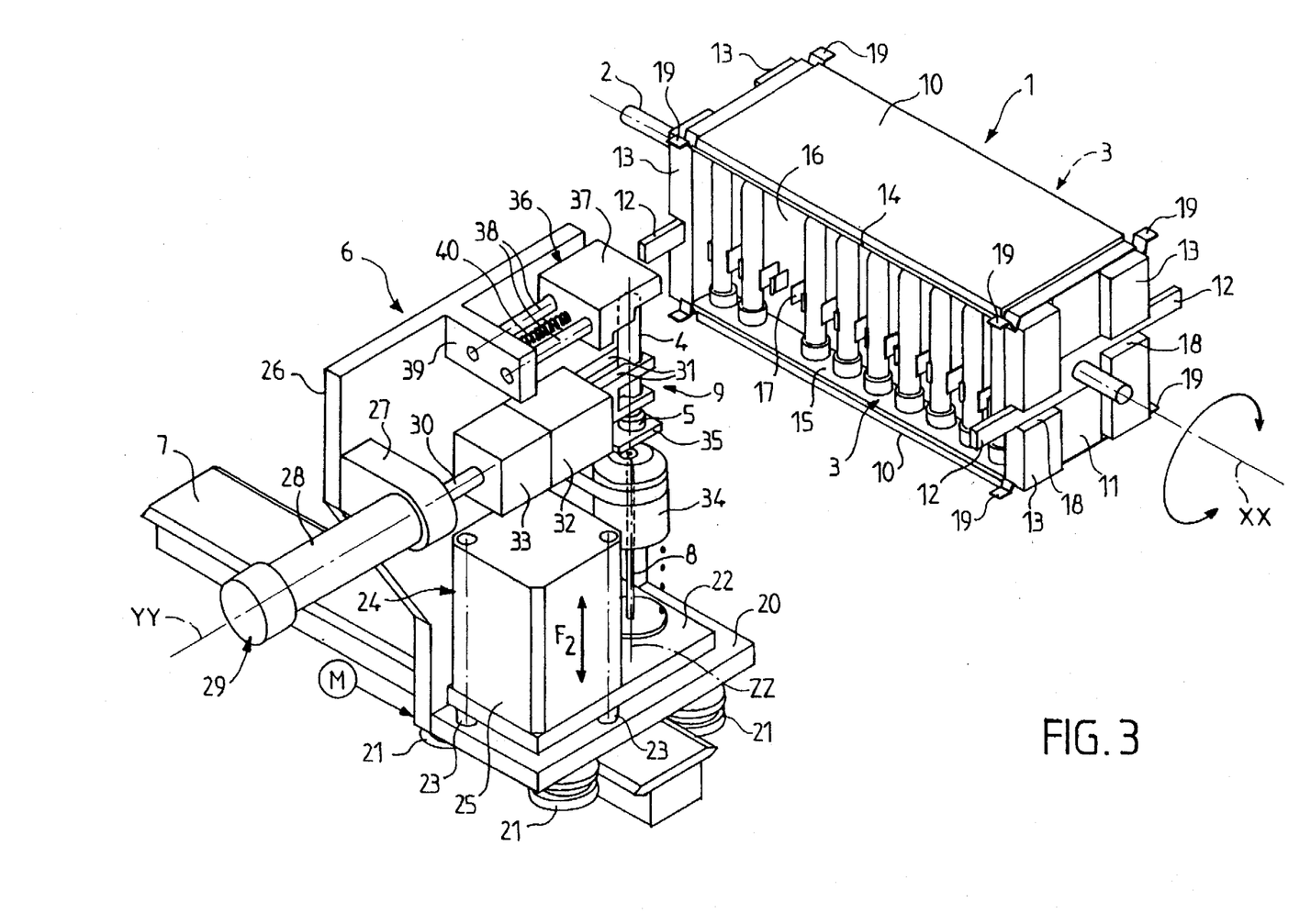

The device represented in FIGS. 1 to 3 comprises a rack support 1 mounted rotatably about a longitudinal shaft 2 of axis XX and capable of holding two racks 3 (only one of which can be seen in FIG. 1) in which a plurality of tubes 4 are disposed and aligned side by side, each of these tubes 4 containing a blood product and being closed by a stopper 5.

The device additionally comprises a sampling station 6 which is displaceable in translation on a slide 7 extending parallel to the axis XX and including a sampling needle 8 which is vertically displaceable and whose tip is directed upward. The sampling station 6 additionally comprises a gripping pincer 9 which is displaceable in translation in an axis direction YY, orthogonal to the axis XX, this pincer 9 being capable of taking hold of a selected tube 4 in one of the racks 3 in order to bring it to the sampling station 6, in the axis of the needle 8, so that the latter removes a sample of blood product by piercing of the stopper and then aspiration, and of then bringing the tube 4 back to the position which it was occupying in the rack 3.

The support 1 essentially comprises two rectangular panels 10 which extend parallel to each other and on either side of the shaft 2, said panels being connected by two end struts 11 which are integral with the rotary shaft 2. The panels 10 and the struts together define two opposite U-shaped cradles forming seats for holding the two racks 3 head-to-tail. In the position in FIG. 1, the tubes 4 of the rack 3 close to the sampling station are in one substantially vertical plane, the stoppers being directed downward, while the tubes in the other rack 3 are in another substantially vertical plane, parallel to the abovementioned plane, the stoppers of the tubes being directed upward. Thus, the tubes are in a nonradial position with respect to the axis xx.

The support 1 additionally includes, at the level of each end strut 11, two guides 12 extending in directions substantially parallel to the panels 10 and serving to guide the racks 3 when these are loaded onto the support 1 or withdrawn therefrom, as is described in the publication WO 93/25,885 which has already been mentioned.

Each of the racks 3 forms a flat recipient which comprises two end plates 13 which are connected to each other by two small bars 14 and 15, and a base 16 on which are mounted U-shaped elastic clips 17 which are capable of holding tubes 4 of different lengths and/or diameters. In this example, each rack can contain ten tubes.

Each of the plates 13 comprises a cutting 18 for the passage of the guides 12. In addition, the support 1 comprises four pairs of elastic clips 19 which are capable of cooperating with the plates 13 of the racks 3 in order to immobilize them with respect to the support. The racks 3 can be loaded automatically onto the support 1 from a loader (not shown) disposed above the support, the latter being in a position such that the guides 12 extend vertically. The racks 3 can also be withdrawn from the support in a substantially horizontal direction when the support occupies the position in FIG. 1, the rack being withdrawn toward the right, that is to say away from the sampling station.

Means permitting the automatic loading and withdrawal of the racks on and from the support are also described in the publication WO 93/25,885 which has already been mentioned.

The support 1 can be driven in rotation about its axis XX by a suitable motor (not shown) in order to communicate to it a complete rotational movement or else alternating rotational movements, and to do this in a controlled manner, so as to agitate the tubes.

The sampling station 6 comprises a base 20 which is displaceable in translation along the slide 7 by way of rollers 21, in one direction or the other, as shown by the double arrow F1. The displacement of the base 20 can be effected by any suitable activator, for example by an electric motor M (not shown) driving in rotation a screw rod (not shown) associated with a nut (not shown) integral with the base 20. The activator is designed to displace the base by increments so as to bring the gripping pincer 9 in a controlled manner into line with a selected tube 4 contained in the rack 3.

The sampling needle 8 is mounted on a deck 22 capable of sliding vertically on guide columns 23, which extend perpendicular to the base 20, under the action of a double-action pneumatic thrustor 24. This thrustor 24 comprises a body 25 mounted on the deck 22, and a rod (not shown) bearing on the base 20. When the rod of the thrustor is deployed, the deck 22 moves away from the base 20 and the needle 8 is displaced vertically upward. Conversely, when the rod of the thrustor is retracted, the deck 22 approaches the base 20 and the needle 8 is displaced vertically downward. The displacement is represented by the double arrow F2 in FIG. 3.

The sampling station 6 additionally comprises a vertical panel 26 attached perpendicular to the base 20 and forming a support for various members of the sampling station. Fixed on the panel 26 is a flange 27 which supports a double-action pneumatic thrustor 29 via its body 28, the rod 30 of which pneumatic thrustor 29 bears, at its free end, the gripping pincer 9. The thrustor 29 thus permits displacement of the gripping pincer in the line of the axis YY, in one direction or the other, so as to displace the pincer either in the direction of the rack 3 or in the direction of the sampling station (double arrow F3 in FIG. 2).

The pincer 9 comprises two jaws 31 capable of being brought together or spaced apart from each other by pivoting about an axis parallel to the direction of the tubes 4. These jaws 31 are mounted on a support 32 borne by the rod 30 of the thrustor and they can be brought together or spaced apart from each other by an activator 33 which, in this example, is a double-action pneumatic thrustor.

The panel 26 of the station 6 additionally bears a rinsing member 34 serving to clean the sampling needle after each sampling operation.

Furthermore, the panel 26 supports a first fixed abutment 35 capable of forming a bearing for the stopper 5 of the tube, when the latter is held in the sampling position in the axis of the needle 8 by the gripping pincer 9. The panel 26 additionally supports a second abutment 36 which is adjustable and is capable of forming a bearing for the bottom of the tube when the latter is held in the sampling position. This second abutment 36 is adjustable in order to adapt automatically to the length of the tube, it being possible for said length to assume values determined in advance. The second abutment 36 comprises a stepped block 37 whose structure will be defined hereinafter. This block 37 is mounted slidably on two guide rods 38 which extend parallel to the axis YY and thus orthogonal to the axis XX, these two rods being supported by a flange 39 attached to the panel 26. An elastic return spring 40 is interposed between the block 37 and the flange 39 in such a way as to stress the block 37 in the direction of the rack support. The block 37 is thus displaceable in translation orthogonal to the axis XX and in both directions, as is shown by the double arrow F4 in FIG. 2.

The operation of the device will now be explained with reference to FIGS. 1 to 3. In the rest position in FIG. 1, the gripping pincer 9 is close to the sampling station 6 and its jaws are open. The sampling station 6 is then displaced in translation along the slide 7 by the motor M (arrow F1) such that the axis YY of displacement of the pincer is situated in line with that tube 4 of the rack 3 which has been selected to be removed. The rack support 1 has been driven in rotation about its axis beforehand in order to agitate all the tubes contained in the rack or racks.

After positioning the sampling station with respect to the slide 7, the rod 30 of the thrustor 29 is deployed in order to position the jaws 31, which are still open, of the gripping pincer 9 around the selected tube, the support 1 being immobilized. In this example, the selected tube is the third tube, counting from the left of the row, as is shown in FIG. 2. The two jaws 31 of the pincer are then brought together by the thrustor 33, as is shown by the arrows F5 in FIG. 2. Thus, the approach movement of the pincer 9 is effected by means of a displacement in a general direction transverse to the axis of the tube, and the tube is gripped from the side. During all the abovementioned displacements, the tube retains substantially the same spatial orientation with its stopper turned downward.

The jaws 31 of the pincer are advantageously made of a flexible material in order to grip the wall of the tube, which is normally made of glass, without breaking it.

The rod 30 of the thrustor 29 is then retracted (arrow F3), which allows the tube 3 to be brought into the sampling position shown in FIG. 3. In this position, the stopper 5 of the tube 4 bears against the fixed abutment 35, and its bottom bears against the adjustable abutment 36. In this same position, the rod of the thrustor 24 is retracted (arrow F2), the sampling needle 8 being in the lower position. The rod of the thrustor 24 is then deployed in order to provoke the upward displacement of the sampling needle 8, such that its tip pierces the stopper 5 in order to permit the removal of a blood product sample by suitable aspiration means (not shown). As soon as this sampling has been carried out, the sampling needle 8 is lowered and the rod of the thrustor 29 is deployed in order to displace the tube 4 and deposit it in the rack in the position it was originally occupying. The gripping pincer then adopts a depositing position which corresponds to the pick-up position in FIG. 2. During replacement of the tube, the clip 17 opens out automatically and subsequently holds the tube in position. The pincer is then returned toward the starting position in FIG. 1, so that the device can be subjected to other similar operating cycles. At the beginning of each new cycle, the sampling station 6 is displaced in translation along the slide 7 so that the gripping pincer 9 is situated facing the selected tube.

Thus, the displacements of the gripping pincer are effected at all times in a direction transverse to the axis of the tube, the latter being taken or replaced by lateral grip. It should be noted that during the actual sampling itself (FIG. 3), the support 1 is normally driven in rotation, which permits agitation of the other tubes.

Figure 4:
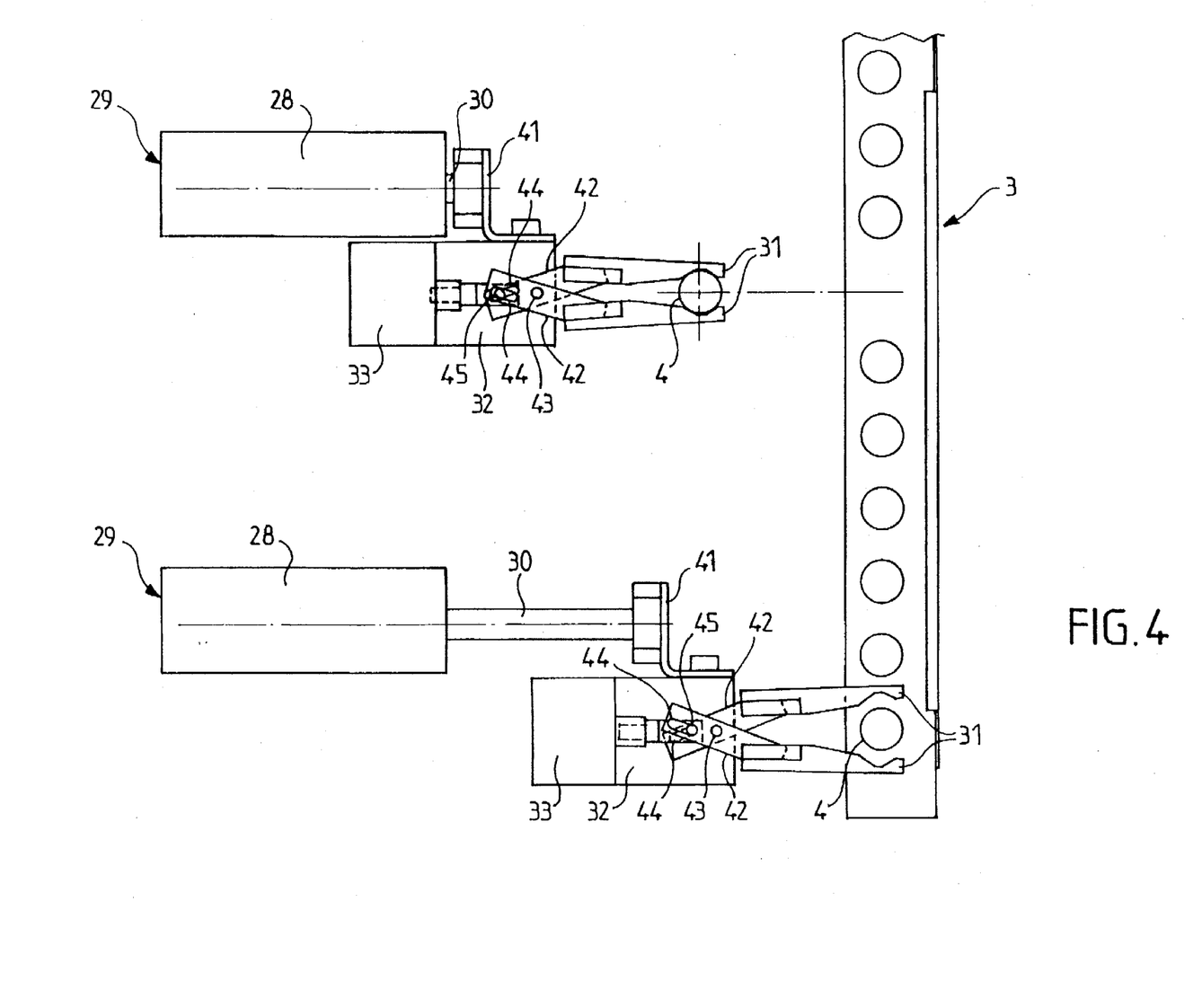
FIG. 4 is a plan view of the gripping means, in the sampling position and in the depositing position, respectively.

Reference is now made to FIG. 4 which represents an alternative embodiment of the gripping pincer 9. According to this alternative, the body 28 of the thrustor 29 is offset laterally with respect to the jaws 31. The rod 30 of the thrustor 28 is coupled to an angle bracket 41 which bears the support 32 on which the activator 33 is mounted on one side and the two jaws 31 of the pincer are mounted on the other side. The two jaws 31 are borne by two crossed levers 42 which are mounted pivotably about a common pivot 43 and have respective oblong openings 44 through which a pin 45 passes, said pin 45 being mounted transverse to the end of the rod of the activator 33. When this rod is retracted, the two pincers are brought together (see upper part of FIG. 4), and when the rod is deployed, the two jaws are opened out (lower part of FIG. 4).

In the upper part of FIG. 4, the two jaws of the pincer are holding the fourth tube, from a row of ten tubes, in the sampling position. In the lower part of FIG. 4, the two jaws 31 are opened out and are ready to take hold of the tenth tube from this row of ten tubes.

When all the tubes in a rack have been withdrawn from the latter and samples have been taken from them, the rack support is turned through 180° in order to bring the other rack into position facing the sampling station, the stoppers of the tubes in this other rack being automatically directed downward. The sampling station and the gripping pincer can be activated again in order to perform analogous operations on the tubes from the second rack.

Figure 5:
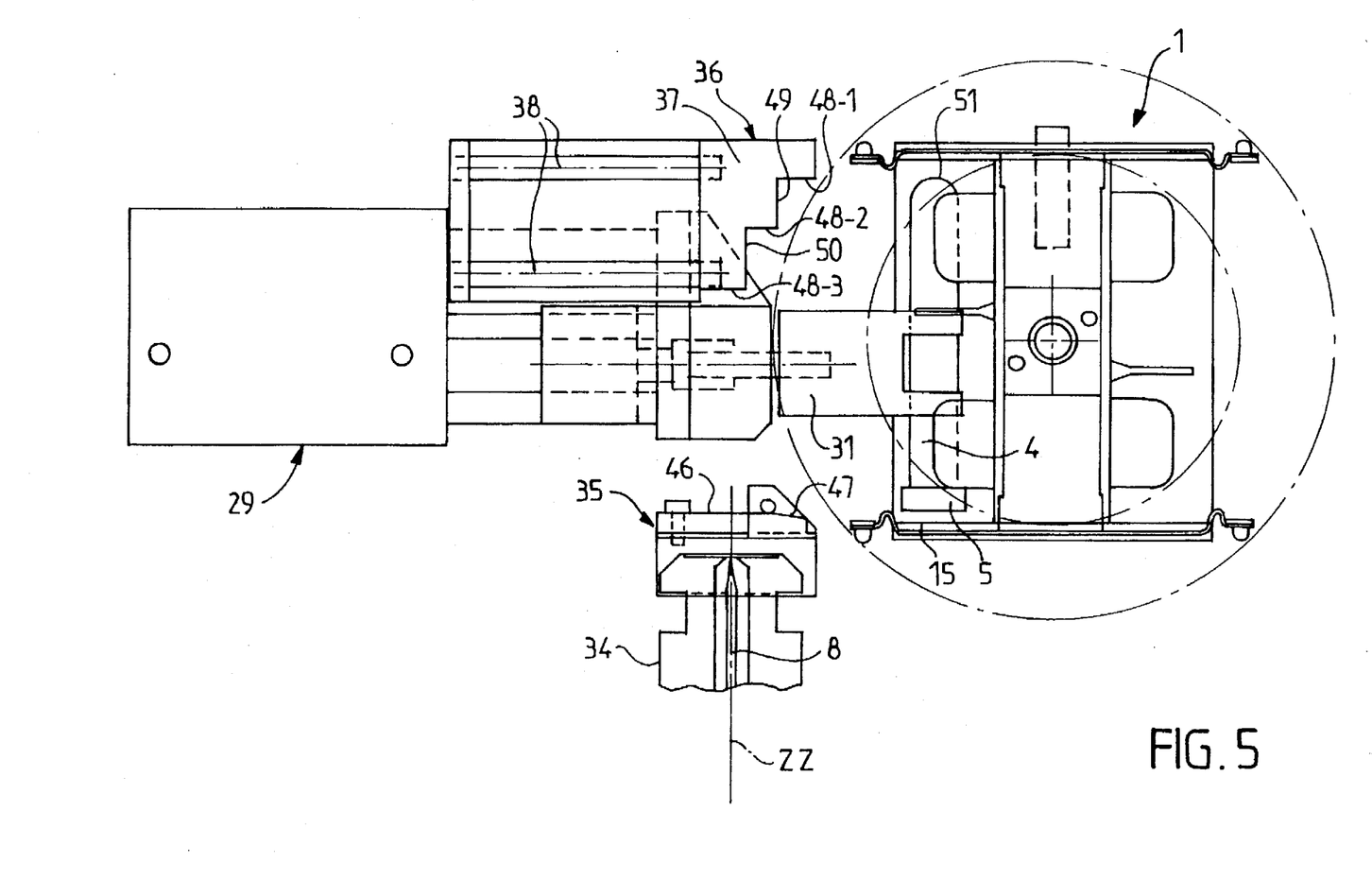
FIG. 5 is a side view of the device, showing the gripping means in the position picking up a tube of long length.

Reference is now made to FIG. 5. The fixed abutment 35 includes a bearing surface 46 which extends perpendicular to the axis ZZ of displacement of the needle 8 and through which the latter can pass. This surface 46 continues laterally, in the rack support direction, via a ramp 47 which facilitates the guidance of the stopper 5 of the tube, as the latter approaches the sampling position in which the axis of the tube is aligned with the axis ZZ of the needle 8. It should be noted that, in the rack 3, the tubes with stoppers 5 always come to rest on the small bar 15, irrespective of the diameter and length of the tubes, so as to provide a positioning indicator.

The stepped block 37 of the adjustable abutment 36 is designed to adapt automatically to tubes of different lengths of given value, in this example three tube lengths: a length L1 (long tubes), a length L2 (medium tubes), and a length L3 (short tubes). To this end, the stepped block 37 includes three bearing surfaces 48-1, 48-2 and 48-3 which present simultaneously a longitudinal offset (parallel to the direction of translation ZZ of the sampling needle) and a lateral offset (perpendicular to the direction of translation ZZ of the needle). The three bearing surfaces 48-1, 48-2 and 48-3 form a sort of stairway and are connected to each other by transverse walls 49 and 50. The distance which separates the plane of the bearing surface 46 from the respective planes of the bearing surfaces 48-1, 48-2 and 48-3 corresponds, respectively, to the lengths L1, L2 and L3 (stoppers included).

Figure 6:
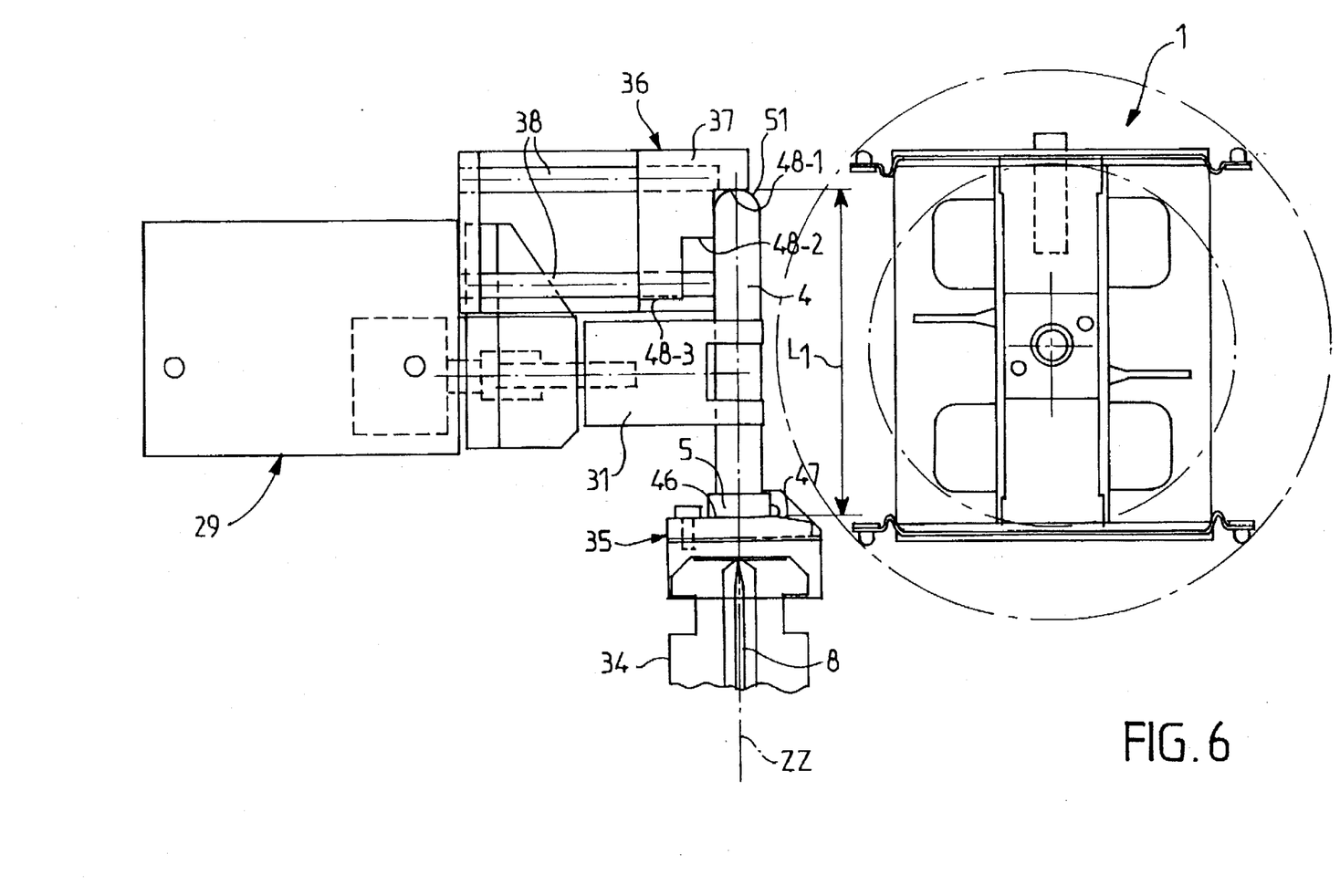
FIG. 6 is a view analogous to that of FIG. 5, in the sampling position.
Figure 7:
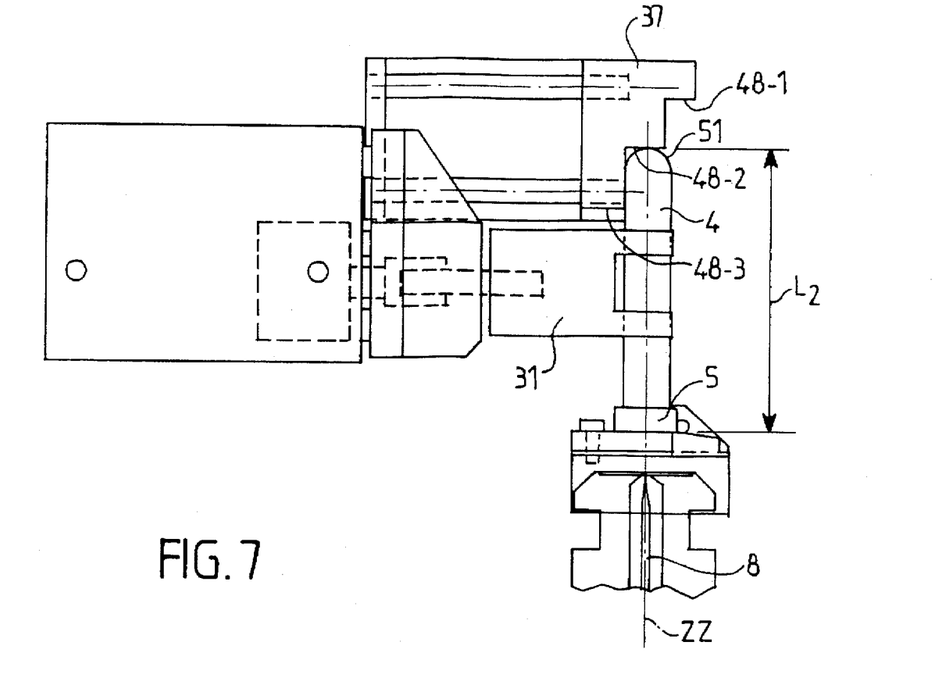
FIGS. 7 and 8 are partial views analogous to those of FIG. 6, showing the device in the sampling position for a tube of average length and a tube of short length, respectively.
Figure 8:
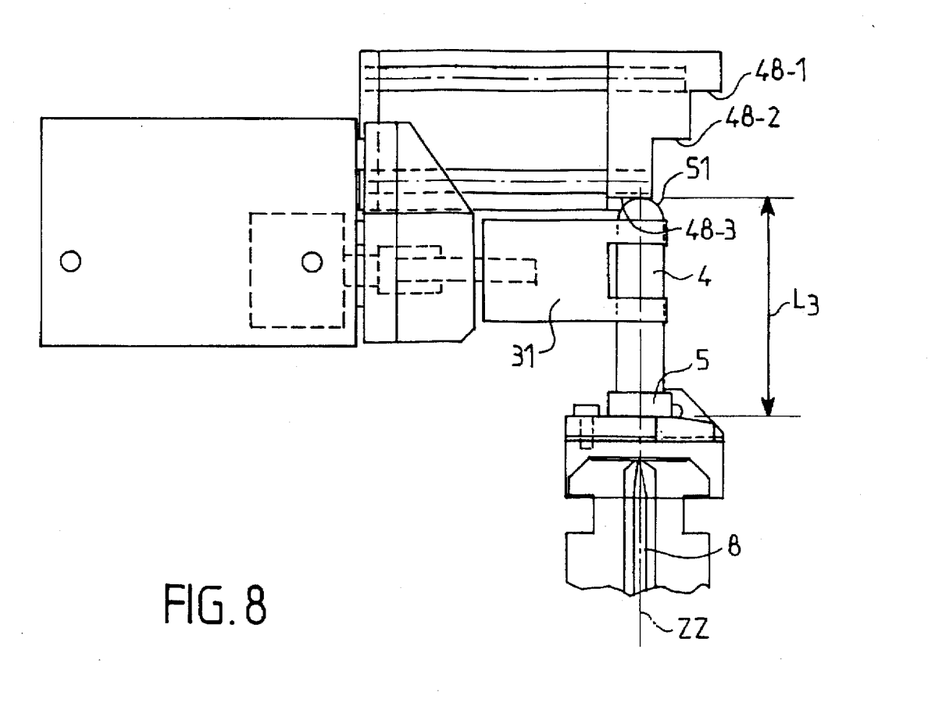

When there is no tube in the sampling position, the bearing surface 48-3 corresponding to the short tubes is situated in the axis of displacement ZZ of the sampling needle (FIG. 5). In this example, the gripping pincot 9 takes hold of a tube 4 of length L1 (FIG. 5) so as to displace it toward the sampling position (FIG. 6). During this displacement, the bottom 51 of the tube 20 comes to bear laterally against the transverse surface 49 of the block 37 and thus to displace this block 37, counter to the force of the spring 40, until the bearing surface 48-1 is situated in the axis of the sampling needle. If a medium-sized tube of length L2 is used, the bottom of the tube comes to bear, during displacement, against the transverse surface 50 and brings the bearing surface 48-2 into the continuation of the axis of displacement ZZ of the needle (FIG. 7).

In the case where the gripping pincer 9 takes hold of a short tube of length L3, the bottom of the tube slides under the bearing surface 48-3 of the block 37, the latter thus not being displaced.

The device according to the invention permits better agitation of the blood products on account of the fact that the rack support can be driven in motion before, during and after the sampling operations. It need only be immobilized temporarily when the gripping means come to take hold of a tube from a rack with a view to taking a sample from it, and when they subsequently come to replace it in the rack, once the sampling has been carried out.

Furthermore, it is not necessary to provide powerful mechanical means for temporarily immobilizing the rack support, on account of the fact that samples are taken from the tubes when outside the rack, and not when in the rack held on the support.

The invention is not limited to the embodiments which have been described hereinabove by way of example. Thus, the gripping means can include one or more gripping pincers for taking hold of one or more tubes at a time from a rack.

The rack support is not necessarily a support mounted rotatably about an axis. It can be another type of support which ensures agitation of the samples by tilting, tipping over or else rotating the tubes about themselves.

Although it is preferable for the tubes to be oriented with their stoppers facing downward for sampling, this arrangement is not compulsory, and it is possible for the stoppers of the tubes to face upward, the sampling needle then being situated above the stopper in the sampling position.

It should be noted that neither are the activating means which displace the gripping means with respect to the support and to the sampling station, limited to the embodiment described above.

Alternatively, the rack support and the sampling station can both be situated at fixed positions in a hematologic analyzer, the drive means then displacing the gripping means in crosswise or orthogonal movements.

In another alternative, the sampling station is at a fixed position in a hematologic analyzer, whereas the rack support is displaceable in this hematologic analyzer, the drive means then comprising first means for displacing the rack support in a direction generally parallel to the direction of alignment of the tubes in the racks, and second means for displacing the gripping means in a direction transverse to the direction of displacement of the rack support.

The gripping means can approach or move away from the selected tube or each selected tube by means of a displacement effected in the axis of the tube and not transverse to this axis, as in the embodiment described by way of example.

In the case where the rack support is adapted to receive a single rack, it is also conceivable for the gripping means to cross the rack in order to pick up one or more tubes as they pass and bring them to the sampling station.

Whatever embodiment is chosen, the activating means can be controlled by a programable automatic unit or any other suitable means.

The device according to the invention can advantageously be combined with automatic transfer means for loading the racks in the support before sampling and then withdrawing them from the support after sampling, as is taught, for example, in the publication WO 93/25,885 which has already been mentioned.

The device according to the invention thus finds an application in hematologic analyzers, such as those used in laboratories, the samples which are taken then being brought into contact with suitable reagents for analysis purposes.

What is claimed is:

1. A device for agitating and taking samples of blood products from tubes which are closed by stoppers and grouped together in a rack, comprising:
    a rack support adapted for holding at least one rack;
    at least one rack held by said rack support and including means for holding a plurality of the tubes, each of the tubes being held in a selected position;
    a sampling station including means for withdrawing a sample of a blood product from a tube at said sampling station;
    gripping means for taking hold and withdrawing from said rack one of said tubes at a selected position, bringing one of said tubes from said selected position to said sampling station and from said sampling station to said selected position without agitation, and replacing said one of said tubes to said selected position;
    drive means for displacing the gripping means; and
    means for agitating said rack support and said at least one rack, said means for agitating being operable during operation of said means for bringing and means for withdrawing.

2. The device as claimed in claim 1, wherein the drive means are displaces the gripping means into the following four successive positions:
    a rest position, in which the gripping means is remote from the rack support;
    a pick-up position, in which the gripping means is close to one of the tubes and is adapted for activation to take hold of the one of the tubes;
    a sampling position, in which the gripping means is close to the sampling station in order to permit sampling from the one of the tubes; and
    a depositing position, in which the gripping means is close to the rack support and is activated in order to release the one of the tubes for replacement in the rack.

3. The device as claimed in claim 1, wherein the gripping means comprises at least one pincer having at least two jaws and activator means for bringing said jaws together or moving said jaws apart from each other.

4. The device as claimed in claim 3, wherein the activator means is a double-action pneumatic thrustor.

5. The device as claimed in claim 1, wherein the rack and the gripping means cooperate such that each of the tubes is held in a direction defined by a longitudinal axis thereof and said gripping means moves in a direction generally transverse to the longitudinal axis.

6. The device as claimed in claim 1, wherein the means for holding comprises a plurality of U-shaped elastic clip means for holding each of the tubes individually and structured for each of the tubes to be withdrawn or put back in place by means of a displacement parallel to said clip means.

7. The device as claimed in claim 1, wherein the rack and the gripping means cooperate such that each of the tubes is held in a direction defined by a longitudinal axis thereof and said gripping means moves along the longitudinal axis.

8. The device as claimed in claim 1, wherein the drive means displaces the gripping means by means of at least one translation, such that one of the tubes held by the gripping means retains a substantially constant spatial orientation.

9. The device as claimed in claim 8, wherein the spatial orientation is the stoppers facing downward.

10. The device as claimed in claim 8, wherein the spatial orientation is the stoppers facing upward.

11. The device as claimed in claim 1, wherein each of said tubes is held in said rack in a direction of alignment, wherein the rack support is disposed in a fixed position in a hematologic analyzer, the sampling station is displaceable in said hematologic analyzer, and wherein the drive means comprises a first means for displacing the sampling station in translation in a direction generally parallel to the direction of alignment, and for bringing the sampling station into line with each of the tubes, and a second means for displacing the gripping means in a direction transverse to the direction of displacement of the sampling station.

12. The device as claimed in claim 11, wherein the first means comprises a slide and a step motor.

13. The device as claimed in claim 11, wherein the second means comprise a double-action pneumatic thrustor.

14. The device as claimed in claim 1, wherein each of said tubes is held in said rack in a direction of alignment, wherein the sampling station is disposed in a fixed position in a hematologic analyzer, and the rack support is displaceable in the hematologic analyzer, and wherein the drive means comprises a first means for displacing the rack support in a direction generally parallel to the direction of alignment, and a second means for displacing the gripping means in a direction transverse to the direction of displacement of the rack support.

15. The device as claimed in claim 1, wherein the rack support and the sampling station are in fixed positions in a hematologic analyzer, and wherein the drive means displaces gripping means in crosswise orthogonal movements.

16. The device as claimed in claim 1, further comprising means for immobilizing the rack support in an off-position, which allows the gripping means to take hold of each of the tubes prior to sampling and subsequently to replace each of the tubes in the rack after sampling, each of the tubes in the rack having a defined orientation.

17. The device as claimed in claim 16, wherein, in the off-position each of the tubes has a substantially vertical orientation, with the stoppers directed downward.

18. The device as claimed in claim 1, wherein the sampling station comprises a sampling needle which is displaceable in translation in a direction along an axis and has a tip capable of piercing the stoppers, a first abutment for forming a bearing for the stoppers of each of the tubes in a sampling position, and a second abutment disposed opposite the first abutment and for forming a bearing for a bottom of each of the tubes held in the sampling position by the gripping means.

19. The device as claimed in claim 18, wherein the second abutment is adjustable in order to adapt to tube length for each of the tubes.

20. The device as claimed in claim 19, wherein the second abutment comprises a stepped block which includes bearing surfaces presenting a longitudinal offset parallel to the direction of translation of the sampling needle, and a lateral offset perpendicular to the direction of translation of the sampling needle, the longitudinal offset allowing the bearing surfaces to adapt to tubes of different lengths.

21. The device as claimed in claim 20, additionally comprising means for elastically stressing the block in a direction toward the rack support, such that the bearing surface, which is nearest the first abutment and which corresponds to a tube of shortest length, is situated in the axis of displacement of the sampling needle.

22. The device as claimed in claim 20, wherein the stepped block includes three bearing surfaces having respective distances from the first abutment which correspond to three tube lengths.

* * * * *